(12) United States Patent
Harris

(10) Patent No.: US 7,767,400 B2
(45) Date of Patent: Aug. 3, 2010

(54) PAIRED-END READS IN SEQUENCING BY SYNTHESIS

(75) Inventor: Timothy D. Harris, Toms River, NJ (US)

(73) Assignee: Helicos Biosciences Corporation, Cambridge, MA (US)

( * ) Notice: Subject to any disclaimer, the term of this patent is extended or adjusted under 35 U.S.C. 154(b) by 0 days.

(21) Appl. No.: 12/025,033

(22) Filed: Feb. 3, 2008

(65) Prior Publication Data

US 2009/0197257 A1    Aug. 6, 2009

(51) Int. Cl.
*C12Q 1/68* (2006.01)
*C12M 1/34* (2006.01)
*C07H 21/04* (2006.01)
*C07H 21/00* (2006.01)
*G01N 31/00* (2006.01)

(52) U.S. Cl. .................. 435/6; 435/287.2; 536/23.1; 536/24.33; 536/25.3; 536/25.32; 702/20

(58) Field of Classification Search ................ None
See application file for complete search history.

(56) References Cited

U.S. PATENT DOCUMENTS

| | | | |
|---|---|---|---|
| 6,210,891 B1 | 4/2001 | Nyren et al. | |
| 6,258,568 B1 | 7/2001 | Nyren | |
| 6,274,320 B1 | 8/2001 | Rothberg et al. | |
| 7,169,560 B2 | 1/2007 | Lapidus et al. | |
| 7,282,337 B1 | 10/2007 | Harris | |
| 7,575,865 B2 * | 8/2009 | Leamon et al. | 435/6 |
| 7,601,499 B2 * | 10/2009 | Berka et al. | 435/6 |
| 2006/0292611 A1 | 12/2006 | Berka et al. | |
| 2007/0070349 A1 | 3/2007 | Harris et al. | |
| 2007/0087362 A1 * | 4/2007 | Church et al. | 435/6 |

FOREIGN PATENT DOCUMENTS

| | | | |
|---|---|---|---|
| WO | WO 2005/003375 A2 * | 1/2005 | |
| WO | WO 2007010252 A1 * | 1/2007 | |
| WO | WO2007120859 | 1/2007 | |

OTHER PUBLICATIONS

Edwards et al.; "Automated DNA Sequencing of the Human HPRT Locus"; Genomics; 6:593-608 (1990).
Karow, Julia; "As Users Demand Paired-End Sequencing, 454, Illumina, and ABI Work on New Kits"; GenomeWeb LLC; print-out (3 pp.) downloaded Oct. 19, 2008 from http://www.in-sequence.com/issues/1_9/features/138789-1. html (2008).
Specification and pending claims from co-pending co-owned U.S. Appl. No. 11/928,695.
Print-out (1 page) downloaded Oct. 19, 2008 from http://yahoo.brand.edgar-online.com/EFX_dll/EDGARpro.dll?FetchFilingHTML1?SessionID=M6WLWdR4tzhwJch&ID=537360; "The Current Genetics and Genome Market—Ample Room for Multiple Players & Applications" marked as Appendix A.
Bennett et al.; "Toward the 1,000 Dollars Human Genome"; Pharmacogenomics, 6:373-382 (2005).
Skiena et al.; Presentation Entitled "Sequence Assembly for Short Paired-Read Technologies"; Department of Computer Science, State University of New York, Stony Brook, NY; (45 pp.); downloaded on Oct. 24, 2008 from http://www.cs.sunysb.edu/.

* cited by examiner

*Primary Examiner*—Bradley L Sisson
(74) *Attorney, Agent, or Firm*—Thomas Meyers; Adam Schoen; Brown Rudnick LLP

(57) ABSTRACT

The disclosure provides methods of generating paired reads in sequencing-by-synthesis process, particularly, in systems with relatively short read lengths (e.g., 15-35bases), such as for example, in single molecule sequencing by synthesis. Several implementations of the methods are provided. Of particular advantage are the methods that permit re-sequencing of the template, which yields lower error rates. The invention further provides methods of using paired reads, for example, for positioning them over repeats or for assembly into large sequences, including whole genome assembly.

32 Claims, 7 Drawing Sheets

US 7,767,400 B2

PAIRED-END READS IN SEQUENCING BY SYNTHESIS

TECHNICAL FIELD

The invention is in the field of molecular biology and relates to methods for nucleic acid analysis. In particular, the invention relates to methods of obtaining paired-end reads on nucleic acid sequencing-by-synthesis platforms.

BACKGROUND OF THE INVENTION

A number of initiatives are currently underway to obtain sequence information directly from millions of individual molecules of DNA in parallel.

The real-time single molecule sequencing-by-synthesis technologies rely on the detection of fluorescent nucleotides as they are incorporated into a nascent strand of DNA that is complementary to the template being sequenced. An example of asynchronous single molecule sequencing by synthesis is illustrated in FIG. 1. As shown, oligonucleotides 30-50 bases in length are covalently anchored at the 5' end to glass cover slips. These anchored strands perform two functions. First, they act as capture sites for the target template strands, if the templates are configured with capture tails complementary to the surface bound oligonucleotides. They also act as primers for the template-directed primer extension that forms the basis of the sequence reading. The capture primers are a fixed position site for sequence determination. Each cycle consists of adding the polymerase-labeled nucleotide analog mixture, rinsing, optically imaging the field containing millions of active primer template duplexes, and chemically cleaving the dye-linker to remove the dye. The cycle (synthesis, detection, and dye removal) is repeated up to 100 times and, possibly, more.

Four major high-throughput sequencing platforms are currently available: the Genome Sequencers from Roche/454 Life Sciences (Margulies et al. (2005) Nature, 437:376-380; U.S. Pat. Nos. 6,274,320; 6,258,568; 6,210,891), the 1G Analyzer from Illumina/Solexa (Bennett et al. (2005) Pharmacogenomics, 6:373-382), the SOLiD system from Applied Biosystems (solid.appliedbiosystems.com), and the Heliscope™ system from Helicos Biosciences (see, e.g., U.S. Patent App. Pub. No. 2007/0070349 and the illustration in FIG. 1). Although these new technologies are significantly cheaper compared to the traditional methods, such as gel/capillary Gilbert-Sanger sequencing, the sequence reads produced by the new technologies are generally much shorter (~25-40 vs. ~500-700 bases). For example, the average read lengths on the four major platforms are currently as follows: Roche/454, 250 bases (depending on the organism); Illumina/Solexa, 25 bases; SOLiD, 35 bases; Heliscope, 25 bases. While such short reads (also referred to as "microreads") are sufficient for the resequencing ~80% of normal human genomes, for which there is a reliable reference sequence, microreads are limiting for a number of other applications. First, short reads are not optimal for the de novo assembly of genomes. Second, the detection and proper placement of amplifications, inversions, and translocations using short reads are severely limited. The proper detection and placement of short indels are also difficult. Short reads may therefore be problematic for the resequencing of highly polymorphic or highly aberrant genomes. For example, the occurrence of Large-scale Copy-number Variations (LCVs) in normal (non-disease) individuals is an indication that acquiring an accurate description of human genetic variation may require more than the detection of single-nucleotide polymorphisms. Genetic rearrangements are even more heterogeneous and prevalent in cancer genomes, underscoring the importance of their proper detection and characterization.

To mitigate the drawbacks of short-read sequencing methods, several groups have proposed to use paired reads, the approach originally developed by Edwards et al. (Genomics (1990) 6: 593-608) for traditional sequencing methods. By linking two reads positioned a certain known distance apart from each other (thus also referred to as "paired," "paired-end," "mate," or "matched" reads), a large informatic leverage is achieved to resolve repeats, insertions, deletions, and inversions, which are important mutation types, for example, in tumors.

In addition to the above limitations of short reads, another inherent disadvantage of single molecule sequencing technologies is a high per-read error rate. This is due to the all-or-none signal detection during an incorporation event and the increased susceptibility to contaminating nucleotides. For instance, the incorporation of an unlabeled nucleotide contaminant in a single nascent strand of complementary DNA will produce a failed detection event or a deletion in the read relative to the reference. Sequencing errors in short reads are especially problematic as they complicate proper alignment of the reads onto a reference sequence. Thus, techniques that allow re-sequencing the original DNA template are preferable because they drastically reduce sequencing errors. See, e.g., WO 2007/12089 and U.S. patent application Ser. No. 11/404,675 for "melt-and-resequence" methods.

Therefore, there is a need for methods of obtaining paired reads in sequencing-by-synthesis technologies, particularly, those with short read lengths, such as produced by single molecule sequencing.

SUMMARY OF THE INVENTION

The invention provides methods of generating paired reads in a sequencing-by-synthesis process, particularly, in systems with relatively short read lengths (e.g., 15-35 bases), such as for example, in single molecule sequencing by synthesis. In such single molecule sequencing methods, the template is individually-optically resolvable. Additional advantages are provided by those methods that permit re-sequencing of the original template, thereby yielding fewer sequencing errors.

In general, the methods of the invention include:
  a) providing a template nucleic acid;
  b) conducting a sequencing-by-synthesis reaction to obtain a first read from the template; and
  c) conducting a sequencing-by-synthesis reaction to obtain a second read from the template.

Both reads (the first and second reads) are separated in the template nucleic acid by a spacer of a defined length (e.g., 20-250). The spacer length may be fixed by the size of the template or it may be dynamically controlled, (e.g., by kinetic control of the polymerization reaction or other methods).

In some embodiments, one or both reads are generated by copying the original template, while in other embodiments one or both reads are generated by copying a copy of the original template. In some embodiments, the reads are generated from the same strand of a nucleic acid duplex, while in other embodiments, the first and second reads are generated from different strands.

In certain embodiments (including Method A as illustrated in FIG. 2), the methods of the invention include:
  i) hybridizing a template to a first universal primer which is attached to a solid support;

ii) obtaining a first read by copying a portion of the template proximal to the support;

iii) extending the copy of the template so as to copy the complement of a second universal priming site located on the distal end of the template;

iv) melting off the template;

v) hybridizing a second universal primer to the copy of the template; and vi) obtaining the second read by copying a portion of the copy of the template, said portion of the copy distal to the support.

In certain other embodiments (including Method B as illustrated in FIG. 3), the methods of the invention include:

i) hybridizing a template to a first universal primer which is attached to a solid support;

ii) obtaining a first read by copying a portion of the template proximal to the support;

iii) further extending the copy of the template thereby creating a spacer; and iv) obtaining the second read by copying a portion of the template distal to the support.

Yet in certain other embodiments (including Methods C and D as illustrated in FIGS. 4 and 5, respectively), the methods of the invention include:

i) covalently attaching a template to a solid support, said template comprising a complement of a universal primer;

ii) hybridizing the universal primer to the template;

iii) obtaining a first read by copying a first portion of the template;

iv) further extending the copy of the template thereby creating a spacer; and v) obtaining a second read by copying a second portion of the template.

In some such embodiments, the template is covalently attached to the support at the 3' end and the universal primer is proximal to the support, whereas in other embodiments, the template is covalently attached to the support at the 5' end and the universal primer is distal to the support.

The invention also provides methods of using the paired reads, for example, for positioning them over repeats or for assembly into large sequences, including whole genome assembly.

DETAILED DESCRIPTION OF THE INVENTION

Figure 1A:
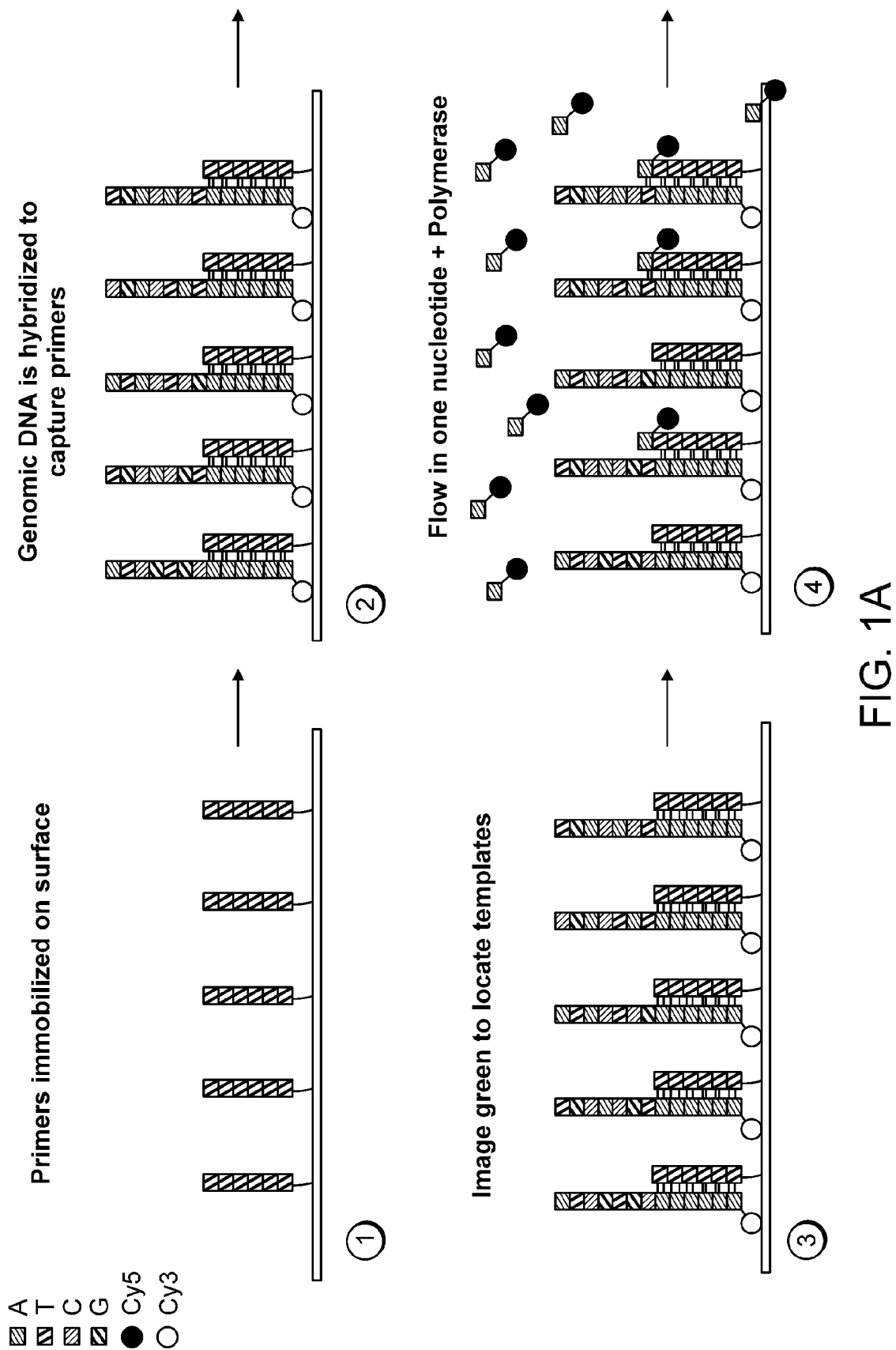
FIGS. 1A and 1B illustrate a typical process of single molecule sequencing by synthesis. 1) "Capture probes" (T(50) oligonucleotides also functioning as primers) are covalently bound with 5' "down" to a surface. 2) Genomic DNA is fragmented, and a polyA tail and a Cy3 label are added at 3' each fragment. These DNA templates are then hybridized to the capture probes. 3) The captured templates are imaged to establish their location. 4) The captured templates are incubated with a Cy5-labeled nucleotide and a polymerase mixture to allow the polymerization reaction to proceed. 5) The surface is rinsed to wash out unincorporated nucleotides and other reagents. 6) The incorporated nucleotides are imaged and associated with each template by their location. 7) The Cy5 label is chemically cleaved off. 8) The process is repeated with another type of nucleotide.
Figure 1B:
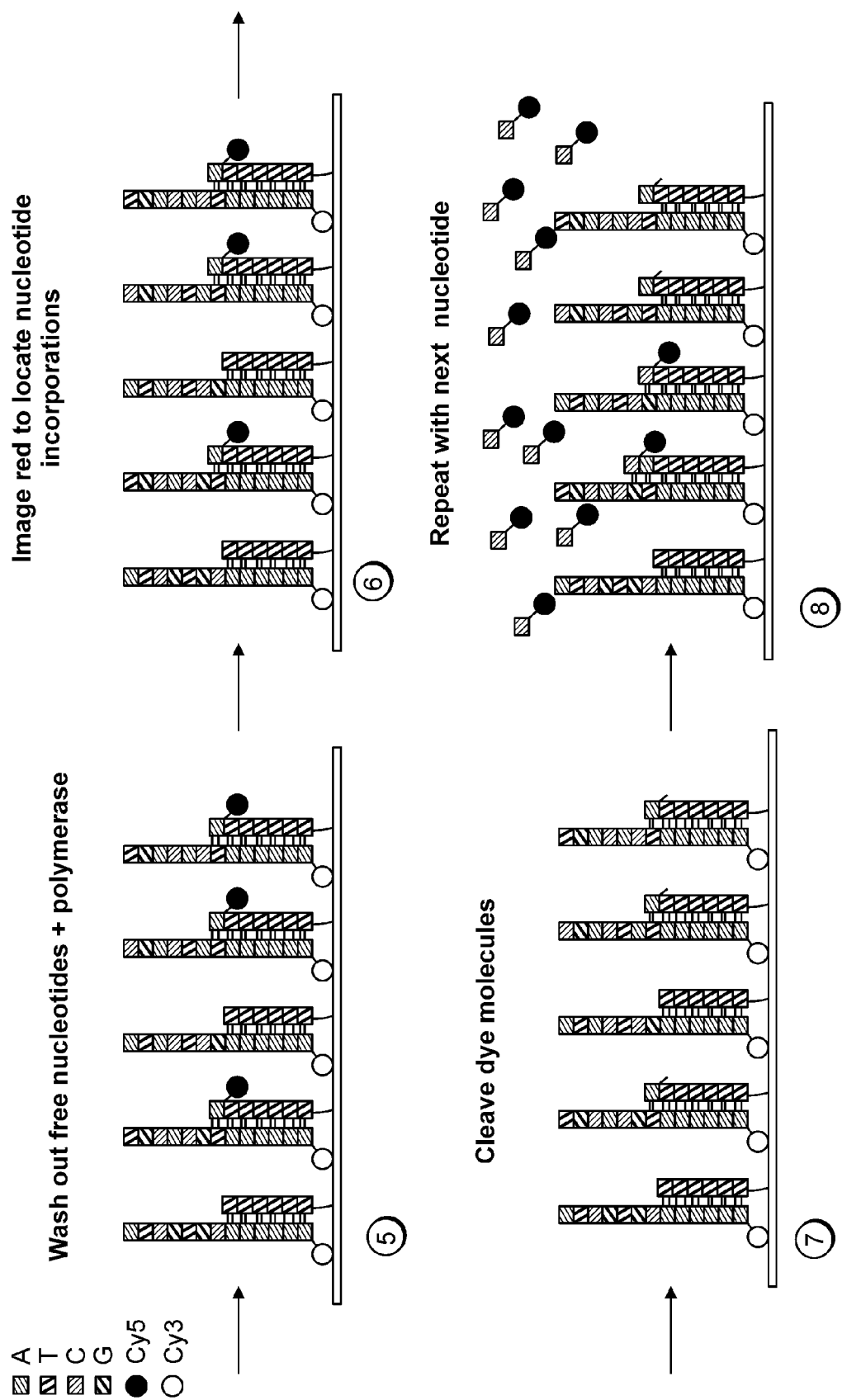

The invention provides methods of generating paired reads from a nucleic acid template in a sequencing-by-synthesis process, wherein the first and second reads are separated in the template nucleic acid by a spacer of a defined length. The invention is suitable for various sequencing-by-synthesis technologies, in particular, the sequencing platforms with relatively short read lengths. In illustrative embodiments, the methods are used in the context of single molecule sequencing as described, for example, in U.S. Pat. No. 7,283,337.

Generally, the methods of the invention include:
a) providing a template nucleic acid;
b) conducting a sequencing-by-synthesis reaction to obtain a first read from the template; and
c) conducting a sequencing-by-synthesis reaction to obtain a second read from the template.

Nonlimiting illustrative embodiments of the invention are shown in FIGS. 2-5 and are described in detail below.

The invention also provides methods of using the paired reads, for example, for positioning them over repeats or for assembly into large sequences, including whole genome assembly. Such methods include mapping the first and second paired reads onto a reference sequence.

In some embodiments, the invention provides additional advantages because it allows resequencing of the reads, thereby reducing the overall error-rate for respective read(s) ("multiple pass reads"). For example, the first and/or the second reads are resequenced multiple times, e.g., once, twice, or more times. In some embodiments, the error rates for single pass sequencing are 3-5% per base, whereas the error rate for two-pass sequencing of the same single molecule is reduced to 0.1-0.25%.

Reads and Spacers

Reads are typically represented by a sequence of detectably labeled nucleotides incorporated into a growing chain of a nucleic acid duplex. Once the nucleotides are incorporated, their labels may remain attached or they may be released. Read lengths (average available read lengths) in the methods of the invention may vary depending on the system used. The first or second read length may be, for example, 5-150, 5-100, 10-75, 15-50, 15-25, 20-35 nucleotides, 50 or fewer, 40 or fewer, 30 or fewer, 25 or fewer, and 20 or fewer nucleotides. (The terms "nucleotide" and "base" in reference to sequence lengths are used interchangeably herein.)

In some embodiments, one or both reads are generated by copying the original template, while in other embodiments, one or both reads are generated by copying a copy of the original template. In some embodiments, the reads are generated from the same strand of a nucleic acid duplex, while in other embodiments, the first and second reads are generated from different strands.

A spacer is typically generated by incorporating nonlabeled (e.g., native) nucleotides into the growing chain. The spacer lengths may vary. As used herein the length of the spacer is defined as the length of sequence between the first and second reads, regardless of whether both reads are generated from the same strand of a nucleic acid or from two different (complementary) strands. In some embodiments, the spacer length is greater than the length of either the first or the second read. The length is "defined" in that it is chosen before obtaining the read(s) and/or is determined after the reads are obtained. For example, the spacer length may be 20-1000, 20-750, 20-500, 30-300, 50-250, 50-150, at least 20 at least 50, at least 75, at least 100, or at least 150 bases long. In various embodiments of the invention, the spacer length can be controlled to ±50%, ±40%, ±30%, ±25% or a lower percent.

Figure 2:
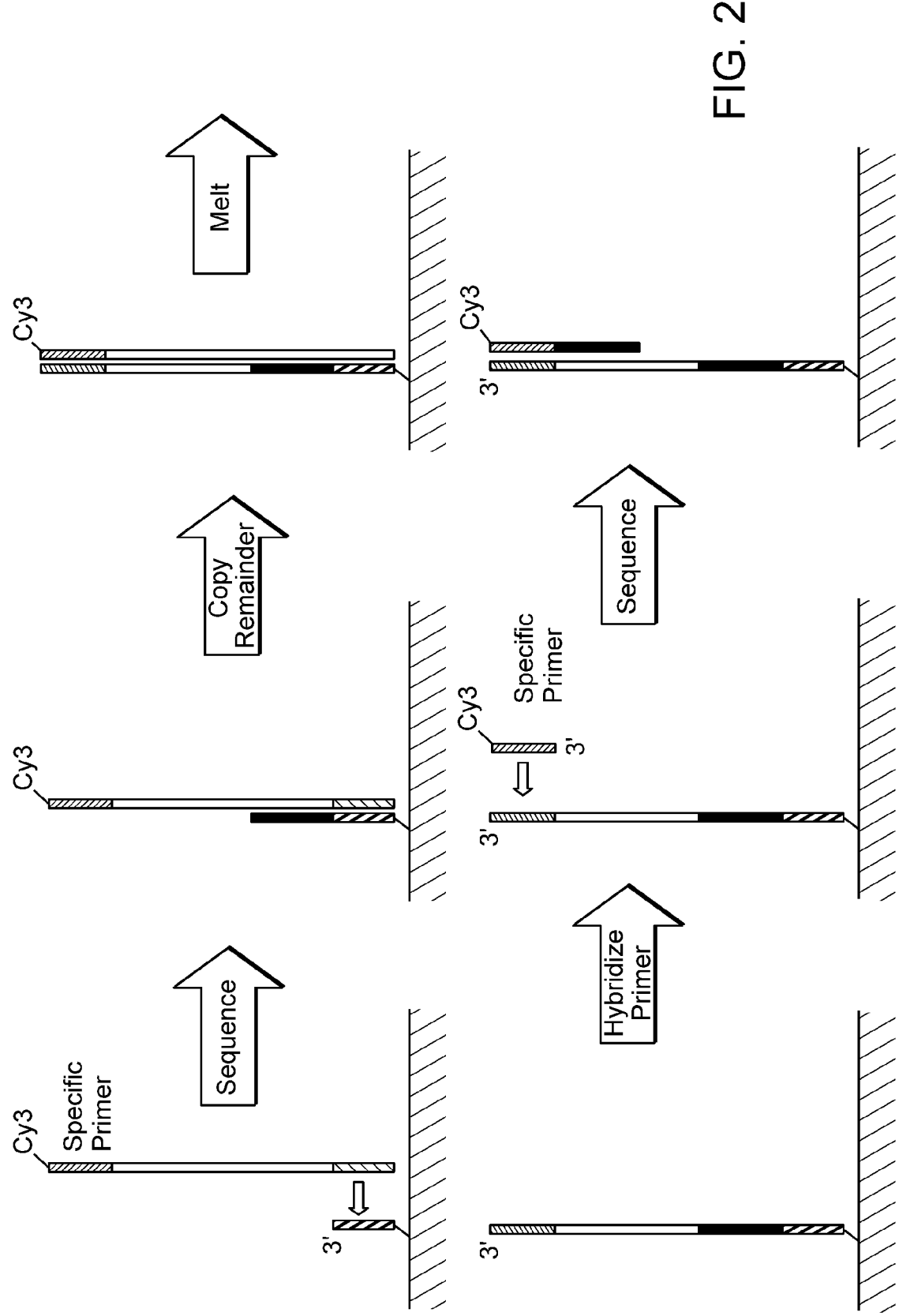
FIG. 2 illustrates a method for generating paired-end reads (Method A), which includes a modified copy step, wherein the spacer length is determined by the size the template. This method allows resequencing of the distal read with a possibility of resequencing the surface proximal read given the proper length of the spacer.

In some embodiments, the spacer length is fixed by the size of the template, for example, when two priming sites are located at each end of the template (see, e.g., FIG. 2). In other embodiments, the spacer length is dynamically controlled (see, e.g., FIGS. 3, 4, and 5). Several methods may be used for the dynamic control of the spacer length. For example, in one method, only one species of the labeled nucleotide is added at a time per incorporation cycles, whereupon its location in the growing chain is detected. (The sequential addition of all four species of labeled nucleotides is referred to as a "quad.") The spacer of desired length may be synthesized by the addition of a pre-determined number of quads coupled with kinetic control of the nucleotide addition by the polymerase, e.g., as described in U.S. Pat. No. 7,169,560. The statistics of spacer length vs. cycle count can be predetermined for a given system and target. Taking M13 genome as an example of genomic sequence, the average distance between G bases is 6 nucleotides with a maximum of 34 bases. If, for example, a long run of AT repeats, sometimes seen in tumors may be encountered, thus a very long spacer would result. If misincorporation can be controlled, variation of the limiting base would allow a useful variety of spacer control statistic to be used. For the G spacer limit chosen above, GC rich regions grow more slowly than AT rich regions, but useful spacer length control is maintained. Under controlled conditions, each incorporation cycle need take no more than a few seconds. Spacer growth may take a minute or two and can be easily automated. An alternative way to dynamically control the spacer length is to use a polymerase in place of the terminal deoxynucleotidyl transferase (TdT), all 4 dNTPs in place of dATP, and duplex templates in place of single-stranded DNA "buffer." A comparable process can be used for control of spacer length. A mixture of nucleotides reflecting the sample composition with the total concentration a factor greater than the template concentration, equal to the desired spacer length may be preferred, or an excess concentration of 3 nucleotides and 1 limiting base may give preferred results. Initiation of synthesis can be controlled with temperature. Other suitable methods for the dynamic control of spacer length may be used.

Specific exemplary embodiments (Methods A-D) are described below.

Method A: Single Pass Reads with Copy to End

One method for generating paired-end reads according to the invention is illustrated in FIG. 2. The first read is obtained using a sequencing-by-synthesis process, and the copy is completed using unlabeled nucleotides. The priming at the 3' end of the anchored copy strand allows the top primer to provide the second read of the pair. Spacer length is determined by the template size. Using size filtration columns, efficient sample handling with sizes 250±100 bases is feasible. However, the approach illustrated in FIG. 2 does not allow both ends of the template to be read more than once. The surface proximal end is read only once.

Accordingly, in some embodiments, the invention provides a method that includes:
i) hybridizing a template to a first universal primer which is attached to a solid support;
ii) obtaining a first read by copying a portion of the template proximal to the support;
iii) extending the copy of the template so as to copy the complement of a second universal priming site located on the distal end of the template;
iv) melting off the template;
v) hybridizing a second universal primer to the copy of the template; and
vi) obtaining a second read by copying a portion of the copy of the template, said portion of the copy distal to the support.

Method B: Single Pass Reads with Variable Spacers

Figure 3:
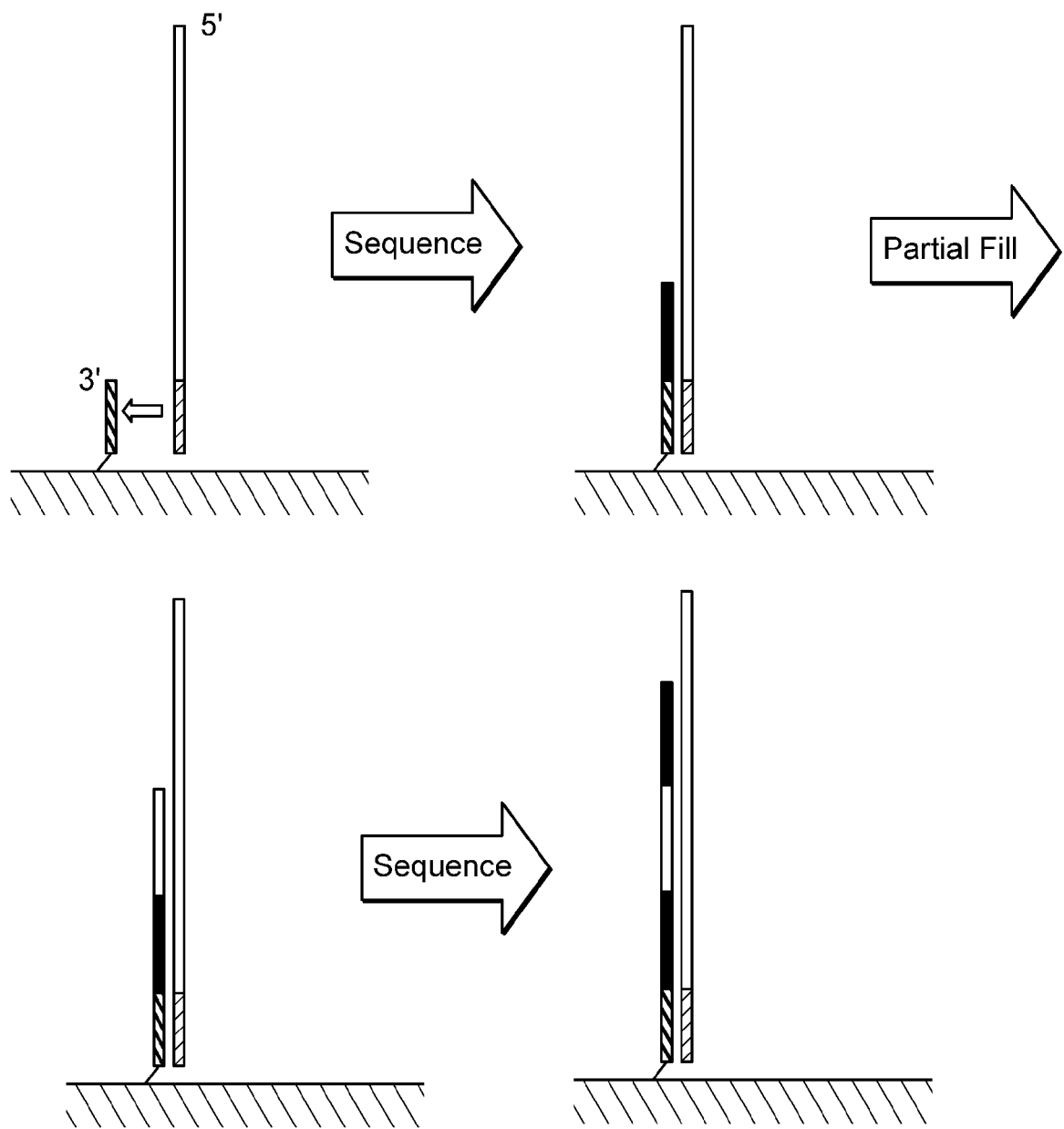
FIG. 3 illustrates a method for generating paired-end reads (Method B) with a 5' non-covalent attachment of the template and a dynamically controlled spacer length. This method does not allow resequencing of the original template.

In the embodiments, such as the one shown in FIG. 3, the template is anchored to the surface and the first read (e.g., the first 15-25 bases) is obtained by a sequencing-by-synthesis process, following which a series of unlabeled bases are added to form a spacer. Then, a second read is obtained by extending the spacer in a second round of sequencing-by-synthesis (with labeled nucleotides). The length of the spacer is dynamically controlled. In some such embodiments, the method of the invention includes the following steps:
i) hybridizing a template to a first universal primer which is attached to a solid support;
ii) obtaining a first read by copying a portion of the template proximal to the support;
iii) further extending the copy of the template thereby creating a spacer; and
iv) obtaining a second read by copying a portion of the template distal to the support.

Method C: Multiple Pass Reads with A 3' Covalent Attachment of Template

Figure 4:
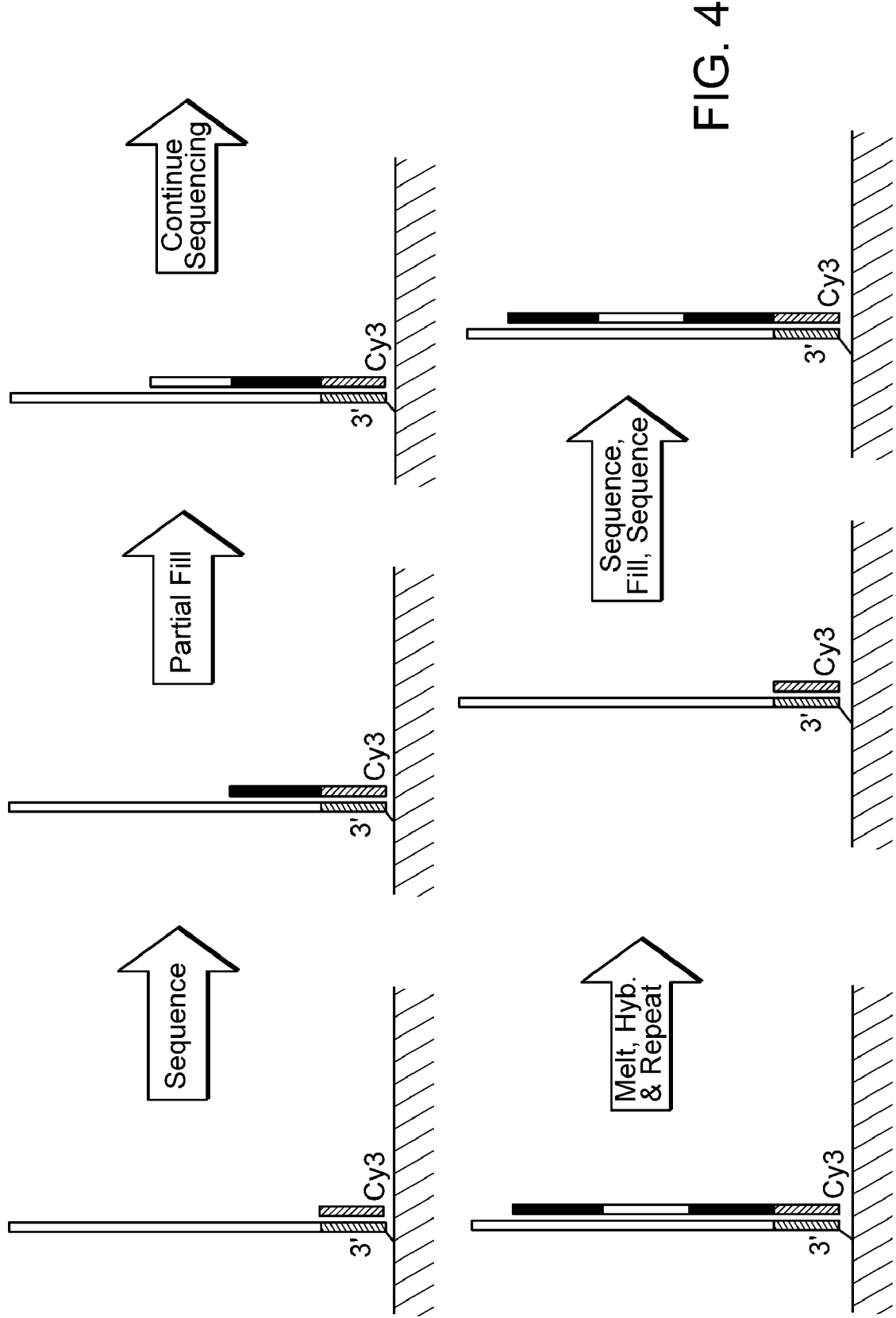
FIG. 4 illustrates a method for generating paired-end reads (Method C) with a 3'-covalently attached template, which allows resequencing.

As illustrated in FIG. 4, the template nucleic can be attached at the 3' end, using click chemistry. This template attachment strategy uses the highly specific reactivity between terminal azide and terminal alkyne groups (see, e.g., Chidsey et al. (2005 JACS, 127:8600 and references cited therein). A first step is to provide a surface with either terminal azide or terminal alkyne groups. Second, the template must be provided with the other member of the click pair, for example, using a nucleotide analog with that group on a suitable linker. One such example is deoxy-adenine triphosphate with a 6-carbon linker terminated with an alkyne. This nucleotide analog can be added to the 3' terminus using d Terminal transferase (dTT) as is done to add labeled diodeoxy 3' terminal bases to these templates. These templates can then be covalently attached to an azide functional surface simply by exposing the surface to the template mixture with the appropriate catalyst.

Accordingly, in some embodiments, the invention provides a method that includes:
i) covalently attaching the template to a solid support at the 3' end (the template contains a universal priming site which is proximal to the support);

ii) hybridizing the universal primer to the template;
iii) obtaining a first read by copying a first portion of the template;
iv) further extending the copy of the template thereby creating a spacer; and
v) obtaining a second read by copying a second portion of the template.

If resequencing is desired, all or a part of the template copy can be removed and steps ii)-v) can be repeated. For example, a copy of the template is melted off. Alternatively, a phosphothioate nucleotide or another nucleotide analog resistant to enzymatic digestion is incorporated in the copy and the respective portion of the copy is removed by enzymatic digestion (e.g., exonuclease digestion). the universal primer may be first capped with a phosphotioate nucleotide. For example, the addition of a phosphothioate terminal nucleotide to the primer allows exonuclease digestion of the copy strand with exception of the primer. Upon digestion, both reads may be resequenced. Yet if only the distal read needs to be resequenced, the phosphotioate may be incorporated immediately before the distal read so that upon exonuclease digestion, solely the distal read may be resequenced. It will be understood that if only a part of the template copy is removed, then only steps iii) through v) or iv) through v) need to be repeated, depending on the position of phosphothioate.

Method D: Multiple Pass Reads with A 5' Covalent Attachment of Template

Figure 5:
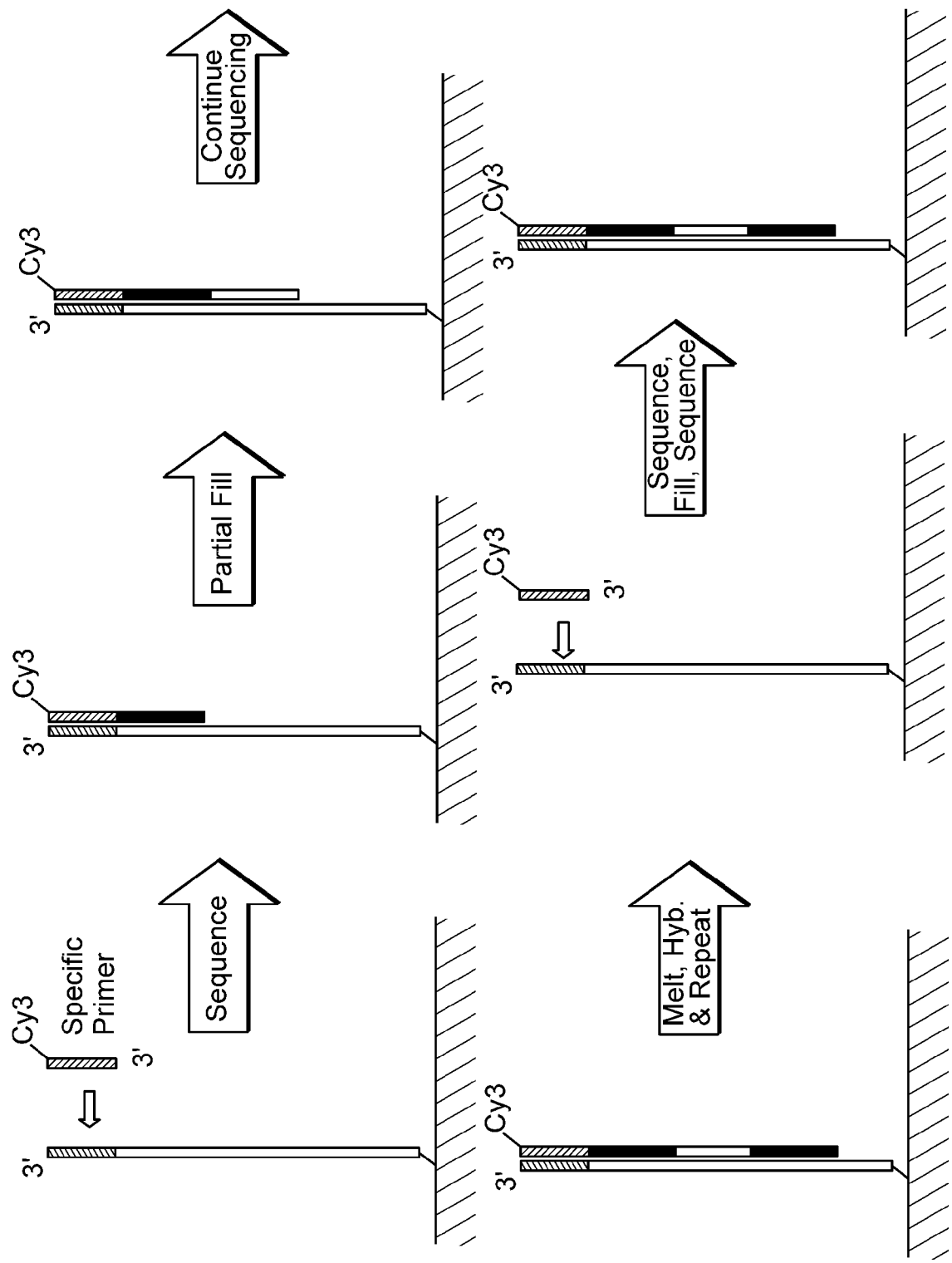
FIG. 5 illustrates a method for generating paired-end reads (Method D) which includes a modified copy step, dynamically controlled spacer length. This method allows re-sequencing of the distal read with a possibility of resequencing the surface-proximal end given the proper length of the spacer.

As illustrated in FIG. 5, the template nucleic can be attached at the 5' end, for example, by an amine linkage.

Accordingly, in some embodiments, the invention provides a method that includes:
i) covalently attaching a template to a solid support at the 5' end (the template contains a universal priming site which is distal to the support);
ii) hybridizing the universal primer to the template;
iii) obtaining a first read by copying a first portion of the template;
iv) further extending the copy of the template thereby creating a spacer; and
v) obtaining a second read by copying a second portion of the template.

Similarly to Method C, all or a part of the template copy can be removed, and the first and/or the second reads may be resequenced.

Nucleic Acid Templates

The length of the target nucleic acid may vary. The average length of the target nucleic acid may be, for example, at least 300, 350, 400, 450, 500, 550, 600, 700, 800, 900, 1000, 2000, 3000, 4000, 5000 nts or longer. In some embodiments, the length of the target is between 300 and 5000 nts, 400 and 4000 nts, or 500 and 3000 nts.

Template nucleic acid can come from a variety of sources. For example, nucleic acids can be naturally occurring DNA or RNA (e.g., mRNA or non-coding RNA) isolated from any source, recombinant molecules, cDNA, or synthetic analogs. For example, the template nucleic acid may include whole genes, gene fragments, exons, introns, regulatory elements (such as promoters, enhancers, initiation and termination regions, expression regulatory factors, expression controls, and other control regions), DNA comprising one or more single-nucleotide polymorphisms (SNPs), allelic variants, and other mutations. The template nucleic acid may also be tRNA, rRNA, ribozymes, splice variants, or antisense RNA.

Template nucleic acid may be obtained from whole organisms, organs, tissues, or cells from different stages of development, differentiation, or disease state, and from different species (human and non-human, including bacteria and virus). Various methods for extraction of nucleic acids from biological samples are known (see, e.g., Nucleic Acids Isolation Methods, Bowein (ed.), American Scientific Publishers, 2002). Typically, genomic DNA is obtained from nuclear extracts that are subjected to mechanical shearing to generate random long fragments. For example, genomic DNA may be extracted from tissue or cells using a Qiagen DNeasy Blood & Tissue Kit following the manufacturer's protocols.

Sequencing platforms

The invention can be used on any suitable sequencing-by-synthesis platform. As described above, four major sequencing-by-synthesis platforms are currently available: the Genome Sequencers from Roche/454 Life Sciences, the 1 G Analyzer from Illumina/Solexa, the SOLiD system from Applied BioSystems, and the Heliscope system from Helicos Biosciences. Each of these platforms can be used in the methods of the invention. In some embodiments, the sequencing platforms used in the methods of the present invention have one or more of the following features:

1) four differently optically labeled nucleotides are utilized (e.g., 1 G Analyzer);
2) sequencing-by-ligation is utilized (e.g., SOLiD);
3) pyrophosphate detection is utilized (e.g., Roche/454); and
4) four identically optically labeled nucleotides are utilized (e.g., Helicos).

Heliscope is the only one of the four systems that provides true single-molecule sequencing (tSMS™), thus eliminating amplification artifacts such as errors or bias. Thus, in some embodiments, the methods of the invention are practiced on a tSMS™ system.

In some embodiments, a plurality of nucleic acid molecules being sequenced is bound to a solid support. To immobilize the nucleic acid on a solid support, a capture sequence/universal priming site can be added at the 3' and/or 5' end of the template. The nucleic acids may be bound to the solid support by hybridizing the capture sequence to a complementary sequence covalently attached to the solid support. The capture sequence (also referred to as a universal capture sequence) is a nucleic acid sequence complimentary to a sequence attached to a solid support that may dually serve as a universal primer. In some embodiments, the capture sequence is $polyN_n$, wherein N is U, A, T, G, or C, $n \geq 5$, e.g., 20-70, 40-60, e.g., about 50. For example, the capture sequence could be $polyT_{40-50}$ or its complement.

As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair.

The solid support may be, for example, a glass surface such as described in, e.g., U.S. Patent App. Pub. No. 2007/0070349. The surface may be coated with an epoxide, polyelectrolyte multilayer, or other coating suitable to bind nucleic acids. In preferred embodiments, the surface is coated with epoxide and a complement of the capture sequence is attached via an amine linkage. The surface may be derivatized with avidin or streptavidin, which can be used to attach to a biotin-bearing target nucleic acid. Alternatively, other coupling pairs, such as antigen/antibody or receptor/ligand pairs, may be used. The surface may be passivated in order to reduce background. Passivation of the epoxide surface can be accomplished by exposing the surface to a molecule that attaches to the open epoxide ring, e.g., amines, phosphates, and detergents.

Subsequent to the capture, the sequence may be analyzed, for example, by single molecule detection/sequencing, e.g., as described in the Example and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or can be done in a step-and-repeat mode. For real-time analysis, different optical labels to each nucleotide may be incorporated and multiple lasers may be utilized for stimulation of incorporated nucleotides.

Other details and variations of the sequencing methods are provided below.

Other General Considerations

A. Nucleotides—Nucleotides useful in the invention include any nucleotide or nucleotide analog, whether naturally occurring or synthetic. For example, preferred nucleotides include phosphate esters of deoxyadenosine, deoxycytidine, deoxyguanosine, deoxythymidine, adenosine, cytidine, guanosine, and uridine. Other nucleotides useful in the invention comprise an adenine, cytosine, guanine, thymine base, a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, and includes chain-terminating analogs. A nucleotide corresponds to a specific nucleotide species if they share base-complementarity with respect to at least one base.

Nucleotides for nucleic acid sequencing according to the invention preferably comprise a detectable label that is directly or indirectly detectable. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes, cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron® Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

B. Nucleic Acid Polymerases—Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al. (1991) Gene, 108:1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh et al. (1977) Biochim. Biophys. Acta, 475:32), *Thermococcus litoralis* (Tli) DNA polymerase (also referred to as Vent® DNA polymerase, Cariello et al. (1991) Polynucleotides Res., 19:4193; New England Biolabs), 9° Nm® DNA polymerase (New England Biolabs), Stoffel fragment, ThermoSequenase® (Amersham Pharmacia Biotech UK), Terminator® (New England Biolabs), *Thermotoga maritima* (Tma) DNA polymerase (Diaz et al. (1998) Braz. J. Med. Res., 31:1239), *Thermus aquaticus* (Taq) DNA polymerase (Chien et al. (1976) J. Bacteoriol., 127:1550), DNA polymerase, *Pyrococcus kodakaraensis* KOD DNA polymerase (Takagi et al. (1997) Appl. Environ. Microbiol., 63:4504), JDF-3 DNA polymerase (from *thermococcus* sp. JDF-3, PCT Patent Application Publication WO 01/32887), *Pyrococcus* GB-D (PGB-D) DNA polymerase (also referred as Deep Vent® DNA polymerase, Juncosa-Ginesta et al. (1994) Biotechniques, 16:820; New England Biolabs), UITma DNA polymerase (from thermophile *Thermotoga maritima*; Diaz et al. (1998) Braz. J. Med. Res., 31:1239; PE Applied Biosystems), Tgo DNA polymerase (from *thermococcus gorgonarius*, Roche Molecular Biochemicals), *E. coli* DNA polymerase I (Lecomte et al. (1983) Polynucleotides Res., 11:7505), T7 DNA polymerase (Nordstrom et al. (1981) J. Biol. Chem., 256:3112), and archaeal DP11/DP2 DNA polymerase II (Cann et al. (1998) Proc. Natl. Acad. Sci. USA, 95:14250-5).

While mesophilic polymerases are contemplated by the invention, preferred polymerases are thermophilic. Thermophilic DNA polymerases include, but are not limited to, ThermoSequenase®, 9°N®, Therminator®, Taq, Tne, Tma, Pfu, Tfl, Tth, Tli, Stoffel fragment, Vent® and Deep Vent® DNA polymerase, KOD DNA polymerase, Tgo, JDF-3, and mutants, variants and derivatives thereof.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin (1997) Cell, 88:5-8; Verma (1977) Biochim. Biophys. Acta, 473:1-38; Wu et al. (1975) CRC Crit. Rev. Biochem, 3:289-347).

C. Surfaces—In a preferred embodiment, nucleic acid template molecules are attached to a solid support ("substrate"). Substrates for use in the invention can be two-or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions which include populations of template nucleic acids or primers. Examples include nucleoside-derivatized CPG and polystyrene slides; derivatized magnetic slides; polystyrene grafted with polyethylene glycol, and the like.

In one embodiment, a substrate is coated to allow optimum optical processing and nucleic acid attachment. Substrates for use in the invention can also be treated to reduce background. Exemplary coatings include epoxides, and derivatized epoxides (e.g., with a binding molecule, such as streptavidin). The surface can also be treated to improve the positioning of attached nucleic acids (e.g., nucleic acid template molecules, primers, or template molecule/primer duplexes) for analysis. As such, a surface according to the invention can be treated with one or more charge layers (e.g., a negative charge) to repel a charged molecule (e.g., a negatively charged labeled nucleotide). For example, a substrate according to the invention can be treated with polyallylamine followed by polyacrylic acid to form a polyelectrolyte multilayer. The carboxyl groups of the polyacrylic acid layer are negatively charged and thus repel negatively charged labeled nucleotides, improving the positioning of the label for detection. Coatings or films applied to the substrate should be able to withstand subsequent treatment steps (e.g., photoexposure, boiling, baking, soaking in warm detergent-containing liquids, and the like) without substantial degradation or disassociation from the substrate.

Examples of substrate coatings include, vapor phase coatings of 3-aminopropyltrimethoxysilane, as applied to glass slide products, for example, from Erie Glass (Portsmouth, N.H.). In addition, generally, hydrophobic substrate coatings and films aid in the uniform distribution of hydrophilic molecules on the substrate surfaces. Importantly, in those embodiments of the invention that employ substrate coatings or films, the coatings or films that are substantially non-interfering with primer extension and detection steps are preferred. Additionally, it is preferable that any coatings or films applied to the substrates either increase template molecule binding to the substrate or, at least, do not substantially impair template binding.

Various methods can be used to anchor or immobilize the primer to the surface of the substrate. The immobilization can be achieved through direct or indirect bonding to the surface. The bonding can be by covalent linkage. See, Joos et al. (1997) Analytical Biochemistry, 247:96-101; Oroskar et al. (1996) Clin. Chem., 42:1547-1555; and Khandjian (1986) Mol. Bio. Rep., 11:107-11. A preferred attachment is direct amine bonding of a terminal nucleotide of the template or the primer to an epoxide integrated on the surface. The bonding also can be through non-covalent linkage. For example, biotin-streptavidin (Taylor et al. (1991) J. Phys. D: Appl. Phys., 24:1443) and digoxigenin with anti-digoxigenin (Smith et al. (1992) Science, 253:11220, are common tools for anchoring nucleic acids to surfaces and parallels. Alternatively, the attachment can be achieved by anchoring a hydrophobic chain into a lipid monolayer or bilayer. Other methods known in the art for attaching nucleic acid molecules to substrates can also be used.

D. Detection—Any detection method may be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091,652). Devices capable of sensing fluorescence from a single molecule include the scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity, Mason (ed.), Academic Press, Landon, pp. 1-11 (1993), such as described in Yershov et al. (1996) Proc. Natl. Acad. Sci., 93:4913, or may be imaged by TV monitoring. For radioactive signals, a PhosphorImager™ device can be used (Johnston et al. (1990) Electrophoresis, 13:566; Drmanac et al. (1992) Electrophoresis, 13:566). Other commercial suppliers of imaging instruments include General Scanning Inc., (Watertown, Mass.; genscan.com), Genix Technologies (Waterloo, Ontario, Canada; confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images ("movies") of fluorophores.

Some embodiments of the present invention use TIRF microscopy for two-dimensional imaging. TIRF microscopy uses totally internally reflected excitation light and is well known in the art. See, e.g., nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

E. Data Analysis, Mapping, and Sequence Assembly—Data analysis of two reads on a single molecule template presents a variety of options. If the two-pass reads differ by more than, for example, 1 or 2 bases the reads should be discarded as arising from unresolved templates or surface contamination near a single template. A composite tag can be constructed of the two or more originating reads, applying high "quality" scores to those bases in agreement. Positioning of the composite tag over the reference can be done with high confidence, assigning any disagreement to a mutation of the sample if a long enough fraction of the tag aligns to give unambiguous alignment. With this exceptional accuracy, ~99.7% or greater, virtually every tag covering a mutation should give the same answer for haploid samples, 50% for diploid samples SNP positions, and an excellent rare mutation detection with coverage as low as 10×. Alternatively, each read of a tag could be aligned separately. These results can be compared to a separate alignment of each individual read over the reference. Positions of agreement within a small error budget, 1 or 2 errors, are scored for best agreements between the tags. A modified Smith-Waterman alignment strategy using the composite tag with base scores may be used. For example paired-end read alignments and assembly, see, e.g., Batzoglou et al. (2002) Genome Res., 12(1):177-189.

The following Example provides illustrative embodiments of the invention and does not in any way limit the invention.

EXAMPLES

Example 1

Single Molecule Sequencing of the M13 Genome

The 7249 nucleotide genome of the bacteriophage M13mp18 was sequenced using a single molecule system of the invention. Purified, single-stranded viral M13mp18 genomic DNA was obtained from New England Biolabs. Approximately 25 µg of M13 DNA was digested to an average fragment size of 250 bp with 0.1 U Dnase I (New England Biolabs) for 10 minutes at 37° C. Digested DNA fragment sizes were estimated by running an aliquot of the digestion mixture on a precast denaturing (TBE-Urea) 10% polyacrylamide gel (Novagen) and staining with SYBR Gold (Invitrogen/Molecular Probes). The DNase I-digested genomic DNA was filtered through a YM10 ultrafiltration spin column (Millipore) to remove small digestion products less than about 30 nt. Approximately 20 pmol of the filtered DNase I digest was then polyadenylated with terminal transferase according to known methods (Roychoudhury, R and Wu, R. 1980, Terminal transferase-catalyzed addition of nucleotides to the 3' termini of DNA. Methods Enzymol. 65(1):43-62). The average dA tail length was 50±5 nucleotides. Terminal transferase was then used to label the fragments with Cy3-ddUTP. The resulting fragments were again filtered with a YM10 ultrafiltration spin column to remove free nucleotides and stored in ddH$_2$O at −20° C.

Epoxide-coated glass slides were prepared for oligo attachment. Epoxide-functionalized 40 mm diameter #1.5 glass cover slips (slides) were obtained from Erie Scientific (Salem, N.H.). The slides were preconditioned by soaking in 3×SSC for 15 minutes at 37° C. Next, a 500 pM aliquot of 5' aminated polydT(50) (polythymidine of 50 bp in length with a 5' terminal amine) was incubated with each slide for 30 minutes at room temperature in a volume of 80 ml. The resulting slides had polydT(50) primer attached by direct amine linkage to the epoxide. The slides were then treated with phosphate (1 M) for 4 hours at room temperature in order to passivate the surface. Slides were then stored in a polymerase rinse buffer (20 mM Tris, 100 mM NaCl, 0.001% Triton X-100 pH 8.0) until they were used for sequencing.

For sequencing, the slides were placed in a modified FCS2 flow cell (Bioptechs, Butler, Pa.) using a 50 µm thick gasket. The flow cell was placed on a movable stage that is part of a high-efficiency fluorescence imaging system built around a Nikon TE-2000 inverted microscope equipped with a total internal reflection (TIR) objective. The slide was then rinsed with HEPES buffer with 100 mM NaCl and equilibrated to a temperature of 50° C. An aliquot of the M13 template fragments described above was diluted in 3×SSC to a final concentration of 1.2 nM. A 100 µl aliquot was placed in the flow cell and incubated on the slide for 15 minutes. After incubation, the flow cell was rinsed with 1×SSC/HEPES/0.1% SDS followed by HEPES/NaCl. A passive vacuum apparatus was used to pull fluid across the flow cell. The resulting slide contained M13 template/oligo(dT) primer duplex. The temperature of the flow cell was then reduced to 37° C. for sequencing and the objective was brought into contact with the flow cell.

For sequencing, cytosine triphosphate, guanidine triphosphate, adenine triphosphate, and uracil triphosphate, each having a cyanine-5 label (at the 7-deaza position for ATP and GTP and at the C5 position for CTP and UTP (PerkinElmer)) were stored separately in buffer containing 20 mM Tris-HCl, pH 8.8, 10 mM MgSO$_4$, 10 mM (NH$_4$)$_2$SO$_4$, 10 mM HCl, and 0.1% Triton X-100, and 100U Klenow exo$^-$ polymerase (NEN). Sequencing proceeded as follows.

First, initial imaging was used to determine the positions of duplex on the epoxide surface. The Cy3 label attached to the M13 templates was imaged by excitation using a laser tuned to 532 nm radiation (Verdi V-2 Laser, Coherent, Inc., Santa Clara, Calif.) in order to establish duplex position. For each slide only single fluorescent molecules that were imaged in this step were counted. Imaging of incorporated nucleotides as described below was accomplished by excitation of a cyanine-5 dye using a 635 nm radiation laser (Coherent). 5 µM Cy5CTP was placed into the flow cell and exposed to the slide for 2 minutes. After incubation, the slide was rinsed in 1×SSC/15 mM HEPES/0.1% SDS/pH 7.0 ("SSC/HEPES/SDS") (15 times in 60 µl volumes each, followed by 150 mM HEPES/150 mM NaCl/pH 7.0 ("HEPES/NaCl") (10 times at 60 µl volumes). An oxygen scavenger containing 30% acetonitrile and scavenger buffer (134 µl HEPES/NaCl, 24 µl 100 mM Trolox in MES, pH6.1, 10 µl DABCO in MES, pH6.1, 8 µl 2M glucose, 20 µl NaI (50 mM stock in water), and 4 µl glucose oxidase) was next added. The slide was then imaged (500 frames) for 0.2 seconds using an Inova 301K laser (Coherent) at 647 nm, followed by green imaging with a Verdi V-2 laser (Coherent) at 532 nm for 2 seconds to confirm duplex position. The positions having detectable fluorescence were recorded. After imaging, the flow cell was rinsed 5 times each with SSC/HEPES/SDS (60 µl) and HEPES/NaCl (60 µl). Next, the cyanine-5 label was cleaved off incorporated CTP by introduction into the flow cell of 50 mM TCEP for 5 minutes, after which the flow cell was rinsed 5 times each with SSC/HEPES/SDS (60 µl) and HEPES/NaCl (60 µl). The remaining nucleotide was capped with 50 mM iodoacetamide for 5 minutes followed by rinsing 5 times each with SSC/HEPES/SDS (60 µl) and HEPES/NaCl (60 µl ). The scavenger was applied again in the manner described above, and the slide was again imaged to determine the effectiveness of the cleave/cap steps and to identify non-incorporated fluorescent objects.

The procedure described above was then conducted with the following addition of nucleotides: 100 nM Cy5dATP, followed by 100 nM Cy5dGTP, and finally 500 nM Cy5dUTP. By far the most common substitution error is G for A in some sequence contexts. This type of misincorporation may be minimized by base addition order, i.e., always adding dATP-Cy5 just before dGTP-Cy5. In this way, the vast majority of "A" sites (T on the template) are filled, thus avoiding such a misincorporation. The procedure (expose to nucleotide, polymerase, rinse, scavenger, image, rinse, cleave, rinse, cap, rinse, scavenger, final image) was repeated as described for ATP, GTP, and UTP except that Cy5dUTP was incubated for 5 minutes instead of 2 minutes. Uridine was used instead of Thymidine due to the fact that the Cy5 label was incorporated at the position normally occupied by the methyl group in Thymidine triphosphate, thus turning the dTTP into dUTP. All 64 cycles (C, A, G, U) were conducted as described in this and the preceding paragraph.

Once 64 cycles were completed, the image stack data (i.e., the single molecule sequences obtained from the various surface-bound duplex) were aligned to the M13 reference sequence. The image data obtained was compressed to collapse homopolymeric regions. Thus, the sequence "TCAAAGC" would be represented as "TCAGC" in the data tags used for alignment. Similarly, homopolymeric regions in the reference sequence were collapsed for alignment. The sequencing protocol described above resulted in an aligned M13 sequence with an accuracy of between 98.8% and 99.96% (depending on depth of coverage). The individual single molecule sequence read lengths obtained ranged from 2 to 33 consecutive nucleotides with about 12.6 consecutive nucleotides being the average length.

The alignment algorithm matched sequences obtained as described above with the actual M13 linear sequence. Placement of obtained sequence on M13 was based upon the best match between the obtained sequence and a portion of M13 of the same length, taking into consideration 0, 1, or 2 possible errors. All obtained 9-mers with 0 errors (meaning that they exactly matched a 9-mer in the M13 reference sequence) were first aligned with M13. Then 10-, 11-, and 12-mers with 0 or 1 error were aligned. Finally, all 11-mers or greater with 0, 1, or 2 errors were aligned. At a coverage depth of greater than or equal to one, 5,001 bases of the 5,066 base M13 collapsed genome were covered at an accuracy of 98.8%. Similarly, at a coverage depth of greater than or equal to five, 83.6% of the genome was covered at an accuracy of 99.3%, at a depth of greater than or equal to ten, 51.9% of the genome was covered at an accuracy of 99.96%. The average coverage depth was 12.6 nucleotides.

Example 2

Length distribution of Strands with Matched Reads

Figure 6:
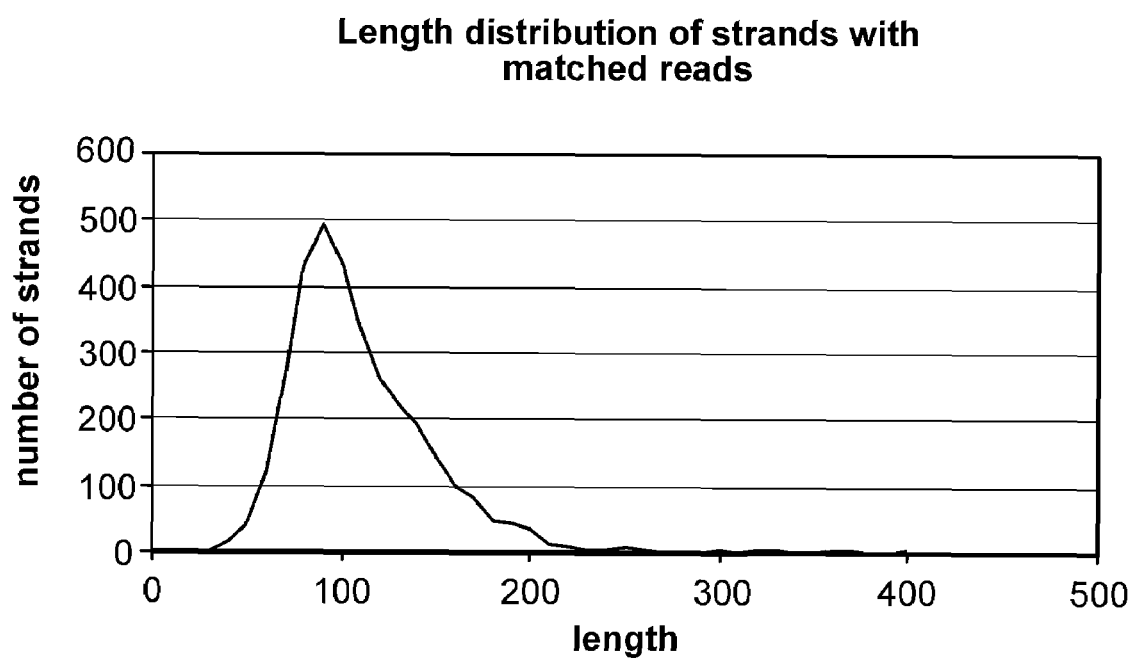
FIG. 6 provides length distribution of paired-end reads obtained using Method A as described in the Examples.

Paired-end reads were obtained using experimental procedures essentially as described in Example 1. The results, representing read length distribution, are shown in FIG. 6, This distribution arises from the spontaneous cessation of sequence accumulation. Two origins are responsible, primer and primer-template loss, dominated by low level nuclease activity, and spontaneous termination of synthesis activity. The loss process is relatively easy to characterize, does not seem to depend on strand growth, and is likely to become insignificant as reagent processing it perfected. The mechanisms of spontaneous termination are less understood at this time. Template damage, either before or caused by the sequencing process does not seem to be a dominant cause. There is some evidence that the residual linker arm after dye cleavage (so-called "scars") may be a substantial factor. The informatic leverage of paired reads, each longer than 30 bases is marginal until those reads exceed ~150 bases. The advantages of these much longer reads for de novo assembly may not be sufficient to justify the system time.

All publications, patents, patent applications, and biological sequences cited in this disclosure are incorporated by reference in their entirety.

The invention claimed is:

1. A method for generating paired reads from a strand of a nucleic acid duplex, the method comprising:
   a) providing a nucleic acid template attached, either directly or indirectly, to a solid support;
   b) conducting a sequencing-by-synthesis reaction using detectably labeled nucleotides to obtain a first read of the template;
   c) synthesizing a spacer of a defined length; and
   d) conducting a sequencing-by-synthesis reaction using detectably labeled nucleotides to obtain a second read of the template, said second read being separated from the first read by the spacer.

2. The method of claim 1, wherein the template is individually optically resolvable.

3. The method of claim 1, further comprising mapping the first and second reads onto a reference sequence.

4. The method of claim 1, wherein the first and/or the second reads are 5-100 nucleotides long.

5. The method of claim 1, wherein the spacer length is greater than the length of the first or the second read.

6. The method of claim 1, wherein the spacer length is 20-1000 nucleotides.

7. The method of claim 1, wherein the spacer length is fixed by the length of the template.

8. The method of claim 1, wherein the spacer length is dynamically controlled.

9. The method of claim 1, wherein the first and/or the second reads are resequenced by a multiple pass sequencing.

10. The method of claim 1, wherein a copy of the template comprises a phosphothioate nucleotide or another nucleotide analog resistant to enzymatic digestion.

11. The method of claim 1, wherein the first and the second reads are obtained from the same copy of the template.

12. The method of claim 1, wherein the first and the second reads are obtained from different copies of the template.

13. The method of claim 1, wherein the template is attached to a solid support at the 5' end that is hybridized to a universal primer covalently attached to the support.

14. The method of claim 13, wherein the universal primer is covalently attached to the support.

15. The method of claim 1, wherein the template is attached to a solid support at the 3' end.

16. The method of claim 15, wherein the template is attached to the support at the 540 end.

17. The method of claim 16, wherein the template comprises a universal primer site at the 3' end.

18. The method of claim 1, wherein the method comprises:
i) hybridizing the template to a first universal primer which is attached to a solid support;
ii) obtaining the first read by copying a portion of the template proximal to the support;
iii) further extending the copy of the template thereby creating the spacer; and
iv) obtaining the second read by copying a distal portion of the template.

19. The method of claim 1, wherein the method comprises:
i) covalently attaching the template to a solid support, said template comprising a complement of a universal primer;
ii) hybridizing the universal primer to the template;
iii) obtaining the first read by copying a first portion of the template;
iv) further extending the copy of the template thereby creating the spacer; and
v) obtaining the second read by copying a second portion of the template.

20. The method of claim 19, wherein the method further comprises melting off the copy of the template and, optionally, repeating steps ii) - v).

21. The method of claim 19, wherein the method further comprises incorporating a phosphothioate nucleotide or another nucleotide analog resistant to enzymatic digestion, performing enzymatic digestion of the copy, and optionally, repeating steps ii) - v).

22. The method of claim 19, wherein the template is covalently attached to the support at the 3' end and the universal primer is proximal to the support.

23. The method of claim 19, wherein the template is covalently attached to the support at the 5' end and the universal primer is distal to the support.

24. The method of claim 19, wherein the length of the spacer is dynamically controlled.

25. The method of claim 1, further comprising resequencing the first and/or the second reads.

26. A method of using paired reads, the method comprising: mapping the paired reads generated by the method of claim 1 onto a reference sequence.

27. The method according to claim 26, wherein using comprises positioning the paired reads over repeats in a reference sequence.

28. The method according to claim 26, wherein using comprises assembling a portion of a genome.

29. The method according to claim 26, wherein using comprises assembling a whole genome.

30. A method for generating paired reads from a strand of a nucleic acid duplex, the method comprising:
a) providing individually optically resolvable nucleic acid templates anchored, directly or indirectly, to a solid support;
b) conducting a sequencing-by-synthesis reaction using detectably labeled nucleotides to obtain a first read of a template, said first read consisting of 20-150 bases;
c) synthesizing a spacer of 20-1000 bases; and
d) conducting a sequencing-by-synthesis reaction using detectably labeled nucleotides to obtain a second read of the template, said second read consisting of 20-150 bases and separated from the first read by the spacer.

31. The method of claim 30, further comprising resequencing the first and/or the second reads prior to the mapping step.

32. A method of using paired reads, the method comprising: mapping the paired reads generated by the method of claim 30 onto a reference sequence.

* * * * *

(12) INTER PARTES REEXAMINATION CERTIFICATE (477th)
United States Patent
Harris

(10) Number: US 7,767,400 C1
(45) Certificate Issued: Oct. 15, 2012

(54) PAIRED-END READS IN SEQUENCING BY SYNTHESIS

(75) Inventor: Timothy D. Harris, Toms River, NJ (US)

(73) Assignee: General Electric Capital Corporation, Bethesda, MD (US)

Reexamination Request:
No. 95/001,530, Jan. 27, 2011

Reexamination Certificate for:
Patent No.: 7,767,400
Issued: Aug. 3, 2010
Appl. No.: 12/025,033
Filed: Feb. 3, 2008

(51) Int. Cl.
*C12Q 1/68* (2006.01)
*C12M 1/34* (2006.01)
*C07H 21/04* (2006.01)
*G01N 31/00* (2006.01)

(52) U.S. Cl. .................. 435/6.11; 435/287.2; 536/23.1; 536/24.33; 536/25.3; 536/25.32; 702/20

(58) Field of Classification Search .................. 435/6
See application file for complete search history.

(56) References Cited

To view the complete listing of prior art documents cited during the proceeding for Reexamination Control Number 95/001,530, please refer to the USPTO's public Patent Application Information Retrieval (PAIR) system under the Display References tab.

*Primary Examiner* — Padmashri Ponnaluri

(57) ABSTRACT

The disclosure provides methods of generating paired reads in sequencing-by-synthesis process, particularly, in systems with relatively short read lengths (e.g., 15-35bases), such as for example, in single molecule sequencing by synthesis. Several implementations of the methods are provided. Of particular advantage are the methods that permit re-sequencing of the template, which yields lower error rates. The invention further provides methods of using paired reads, for example, for positioning them over repeats or for assembly into large sequences, including whole genome assembly.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-32 are cancelled.

* * * * *